(12) United States Patent
Stout

(10) Patent No.: US 9,339,411 B2
(45) Date of Patent: May 17, 2016

(54) STABILIZED HANDLE DESIGN

(71) Applicant: Bayer HealthCare LLC, Whippany, NJ (US)

(72) Inventor: Christopher A. Stout, San Bruno, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 264 days.

(21) Appl. No.: 13/794,223

(22) Filed: Mar. 11, 2013

(65) Prior Publication Data

US 2014/0257034 A1    Sep. 11, 2014

(51) Int. Cl.
*A61F 6/06* (2006.01)
*A61F 6/22* (2006.01)
*A61B 1/018* (2006.01)
*A61B 1/00* (2006.01)

(52) U.S. Cl.
CPC ............. *A61F 6/225* (2013.01); *A61B 1/00066* (2013.01); *A61B 1/018* (2013.01)

(58) Field of Classification Search
CPC ............ A61F 2002/91516; A61F 2002/91533; A61F 2002/91575; A61F 2002/9517; A61F 2230/0013; A61F 2/91; A61F 2/915; A61F 2/95; A61F 6/225; A61F 1/018; A61F 1/00066; A61B 17/0057; A61B 17/0469; A61B 2017/00663; A61B 2017/0472; A61B 2017/00668; A61B 17/3207; A61B 2017/0065; A61B 2017/00654; A61B 2017/00778; A61B 2017/00986; A61B 2017/0477; A61B 2017/12127; A61B 2017/22021; A61B 2017/4233; A61B 2018/00648; A61B 2018/00797; A61B 2019/307; A61B 5/4839; A61B 17/00491; A61B 17/0482; A61B 17/0483; A61B 17/0625; A61B 18/1492; A61B 18/08; A61B 2018/046; A61B 2019/4857; A61B 18/082; A61B 18/20; A61B 18/24; A61B 19/54; A61B 2017/00026; A61B 2017/00084; A61B 2017/00119; A61B 2017/00123
USPC ........... 128/830–831; 606/139, 144, 148, 150
See application file for complete search history.

(56) References Cited

U.S. PATENT DOCUMENTS

| | | | |
|---|---|---|---|
| 6,526,979 B1 | 3/2003 | Nikolchev et al. | |
| 6,634,361 B1 | 10/2003 | Nikolchev et al. | |
| 6,705,323 B1 | 3/2004 | Nikolchev et al. | |
| 6,709,677 B2 | 3/2004 | Baichwal | |
| 6,733,500 B2* | 5/2004 | Kelley et al. | 606/41 |
| 7,918,863 B2 | 4/2011 | Nguyen et al. | |
| 8,360,064 B2 | 1/2013 | Swann et al. | |
| 8,381,733 B2* | 2/2013 | Lowe et al. | 128/830 |
| 8,434,489 B2 | 5/2013 | Gopal et al. | |
| 8,574,245 B2* | 11/2013 | Garrison et al. | 606/148 |
| 8,695,604 B2* | 4/2014 | Lowe et al. | 128/830 |
| 2005/0288551 A1* | 12/2005 | Callister et al. | 600/115 |

OTHER PUBLICATIONS essure™ Permanent Birth Control System, Instructions for Use, Professional Lable, 36 pgs. (Dec. 18, 2002).
essure® Permanent Birth Control System, Instructions for Use, 10 pgs.

* cited by examiner

*Primary Examiner* — Michael Brown

(57) ABSTRACT

The various embodiments of the present invention provide delivery systems and methods of using the delivery systems. The delivery systems facilitate stabilization of a handle assembly against an endoscope during deployment of an occlusion device.

18 Claims, 19 Drawing Sheets

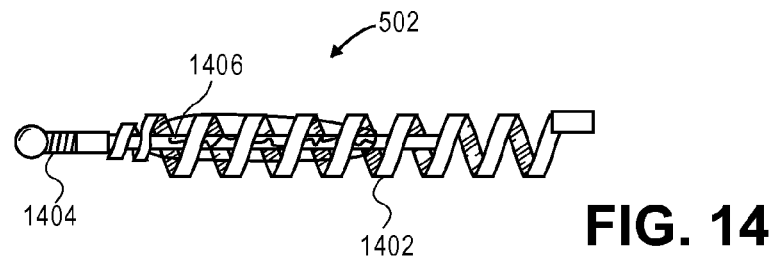
FIG. 14
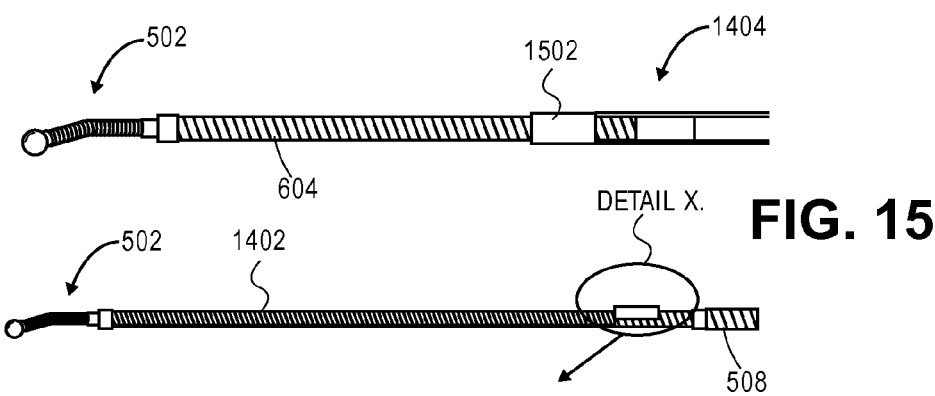
FIG. 15
FIG. 16A
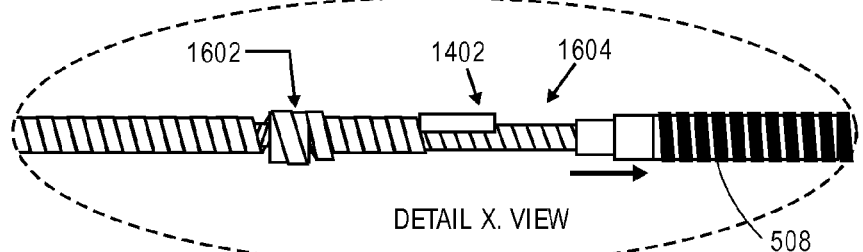
FIG. 16B
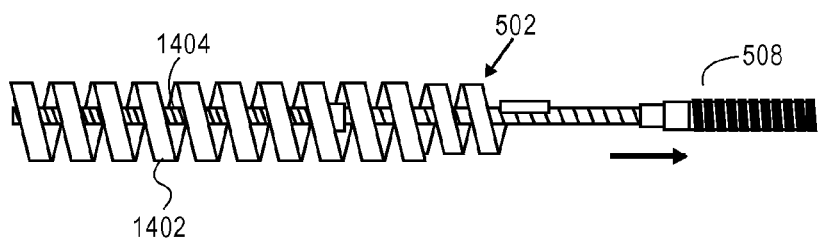
FIG. 17

STABILIZED HANDLE DESIGN

BACKGROUND OF THE INVENTION

1. Field of the Invention

Embodiments of the present invention relate to the field of minimally invasive surgical medical devices and medical procedures. More specifically, embodiments of the present invention relate to devices and methods used for transcervical gynecological procedures.

2. Discussion of Related Art

Female contraception and sterilization may be enabled by transcervically introduced fallopian tube inserts. Devices, systems and methods for contraceptive approaches have been described in various patents and patent applications assigned to the present assignee. For example, U.S. Pat. No. 6,526,979, U.S. Pat. No. 6,634,361, U.S. patent application Ser. No. 11/165,733 published as U.S. Publication No. 2006/0293560, and U.S. patent application Ser. No. 12/605,304 describe transcervically introducing an insert (also referred to as implant and device) through an ostium of a fallopian tube and mechanically anchoring the insert within the fallopian tube. One example of such an assembly is known as "Essure"®, manufactured by Conceptus, Inc. of Mountain View, Calif. Tissue in-growth into the Essure® insert induces long-term contraception and/or permanent sterilization.

Referring to FIG. 1, an illustration of a delivery system is shown. The delivery system 100 may be used to insert an implant similar to that of the Essure® device. The delivery system 100 may include a control device, such as a handle assembly 102, a delivery catheter 104, and a guidewire 106. The contraceptive implant may be held within delivery catheter 104 and/or on guidewire 106 to be placed within a fallopian tube. For example, delivery catheter 104 includes an outer catheter sheathing the implant prior to deployment.

Referring to FIG. 2, an illustration of a delivery catheter of a delivery system before insertion into an endoscope is shown. The delivery catheter 104 may be advanced through a distension valve 202, or similar entrance, into a working channel 204 of an endoscope 206, such as a hysteroscope. Afterward, delivery catheter 104 may be transcervically positioned in a fallopian tube or other target anatomy vian endoscope 206. That is, endoscope 206 may be used to facilitate passage of delivery catheter 104 into a patient and be used to view placement of delivery catheter 104.

Referring to FIG. 3, an illustration of a physician deploying a contraceptive implant according to an instruction for use is shown. Once a physician has positioned the delivery catheter 104 within the fallopian tube for the contraceptive implant to be deposited, a physician can deploy the insert into the fallopian tube by actuating handle assembly 102. For example, the physician may rotate a thumbwheel 302 to deploy the insert from delivery catheter 104. Since delivery catheter 104 can move relative to endoscope 206 during deployment, and because such movement may result in inadvertent repositioning of the insert within the fallopian tube (as well as inaccurate deployment of the insert), the physician may be instructed to hold endoscope 206 and handle assembly 102 simultaneously with a first hand 304. Grasping these components simultaneously with first hand 304 may reduce relative movement between endoscope 206 and handle assembly 102, and therefore stabilize delivery catheter 104 within the fallopian tube. In the stabilized condition, the physician may use a second hand 306 to rotate thumbwheel 302 and accurately deploy the insert at the intended location in the fallopian.

SUMMARY OF THE DESCRIPTION

Delivery systems and methods of using the delivery systems to facilitate stabilization of a handle assembly against an endoscope during deployment of an occlusion device are disclosed. In an embodiment, a delivery system includes an occlusion device, a delivery catheter, and a handle assembly. The delivery catheter may include an outer sheath and a delivery wire. The handle assembly may include a distal handle slidably receiving a proximal handle such that the proximal handle moves relative to the distal handle through a first travel and a second travel. In an embodiment, relative movement between the proximal handle and the distal handle through the first travel retracts the outer sheath over the occlusion device and relative movement through the second travel retracts the delivery wire from the occlusion device. For example, during movement through the first travel, the proximal handle may be operably coupled with the outer sheath and the distal handle may be operably coupled with the delivery wire. Furthermore, during movement through the second travel, the proximal handle may be operably coupled with the outer sheath and the delivery wire.

In an embodiment, the distal handle and the proximal handle may be coaxially arranged with at least a portion of the proximal handle exposed from the distal handle. In an embodiment, the distal handle includes a channel defining the first travel and the second travel and the proximal handle includes a nib slidably located in the channel. In an embodiment, the first travel is in an axial direction. In various embodiments, the second travel may be in a rotational direction or in an axial direction. Furthermore, the proximal handle may be moveable relative to the distal handle through an intermediate travel between the first travel and the second travel, and the intermediate travel may be in a circumferential direction.

In an embodiment, the delivery catheter may include an inner catheter that is operably coupled with the distal handle during the first travel and the second travel. Furthermore, relative movement between the proximal handle and the distal handle through the first travel and the second travel may press the inner catheter against the occlusion device.

In an embodiment, the delivery system may include a sleeve over a gripping surface of the distal handle. The sleeve may have a flexible element normally biased away from the gripping surface. Furthermore, the flexible element may deform toward the gripping surface under a lateral load.

In an embodiment, a method includes inserting a delivery catheter of a delivery system into a lumen of an endoscope and positioning an occlusion device of the delivery system in a body lumen. The method may also include moving a proximal handle of the delivery system relative to a distal handle of the delivery system through a first travel with a first hand, while simultaneously grasping the endoscope and the distal handle with a second hand, to expose the occlusion device to the body lumen. For example, moving the proximal handle through the first travel may include pulling the proximal handle relative to the distal handle. Furthermore, the method may include moving the proximal handle relative to the distal handle through a second travel, while simultaneously grasping the endoscope and the distal handle, to expand the occlusion device into the body lumen. For example, moving the proximal handle through the second travel may include twisting or pulling the proximal handle relative to the distal handle.

In an embodiment, the method may also include moving the proximal handle relative to the distal handle through an intermediate travel between the first travel and the second travel, while simultaneously grasping the endoscope and the distal handle. For example, moving the proximal handle through the intermediate travel may include twisting the proximal handle relative to the distal handle.

In an embodiment, the method includes repositioning the occlusion device in the body lumen after moving the proximal handle through the first travel and before moving the proximal handle through the second travel. For example, grasping the distal handle during the first travel and the second travel may include squeezing a flexible element of a sleeve against the distal handle, and repositioning the occlusion device may include releasing the sleeve from the distal handle.

BRIEF DESCRIPTION OF THE DRAWINGS

The present invention is illustrated by way of example and not limitation in the figures of the accompanying drawings in which like references indicate similar, but not necessarily identical, elements.

FIG. 14 is a side view of an occlusion device in an expanded configuration in accordance with an embodiment of the invention.

FIG. 15 is a side view of an occlusion device in an unexpanded configuration coupled with a delivery catheter in accordance with an embodiment of the invention.

FIG. 16A is a side view of an occlusion device in an unexpanded configuration coupled with a delivery catheter with a retracted outer catheter in accordance with an embodiment of the invention.

FIG. 16B is a detail view, taken of Detail X in FIG. 16A, of an occlusion device in an unexpanded configuration coupled with a delivery catheter with a retracted outer catheter in accordance with an embodiment of the invention.

FIG. 17 is a side view of an occlusion device in a partially expanded configuration coupled with a delivery catheter in accordance with an embodiment of the invention.

DETAILED DESCRIPTION

Various embodiments and aspects of the invention will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the invention. However, in certain instances, well-known or conventional details are not described in order to provide a concise discussion of embodiments of the present invention.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment. Although the processes are described below in terms of some sequential operations, it should be appreciated that some of the operations described may be performed in a different order. Moreover, some operations may be performed simultaneously rather than sequentially.

Figure 1:
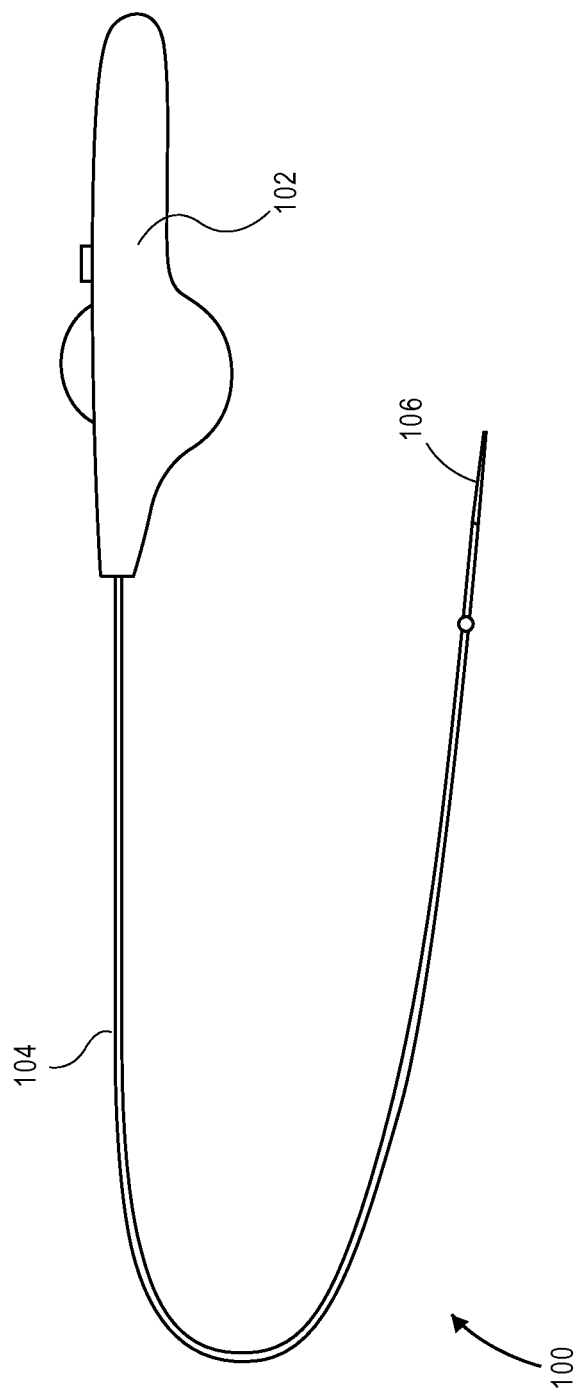
FIG. 1 is an illustration of a delivery system.
Figure 2:
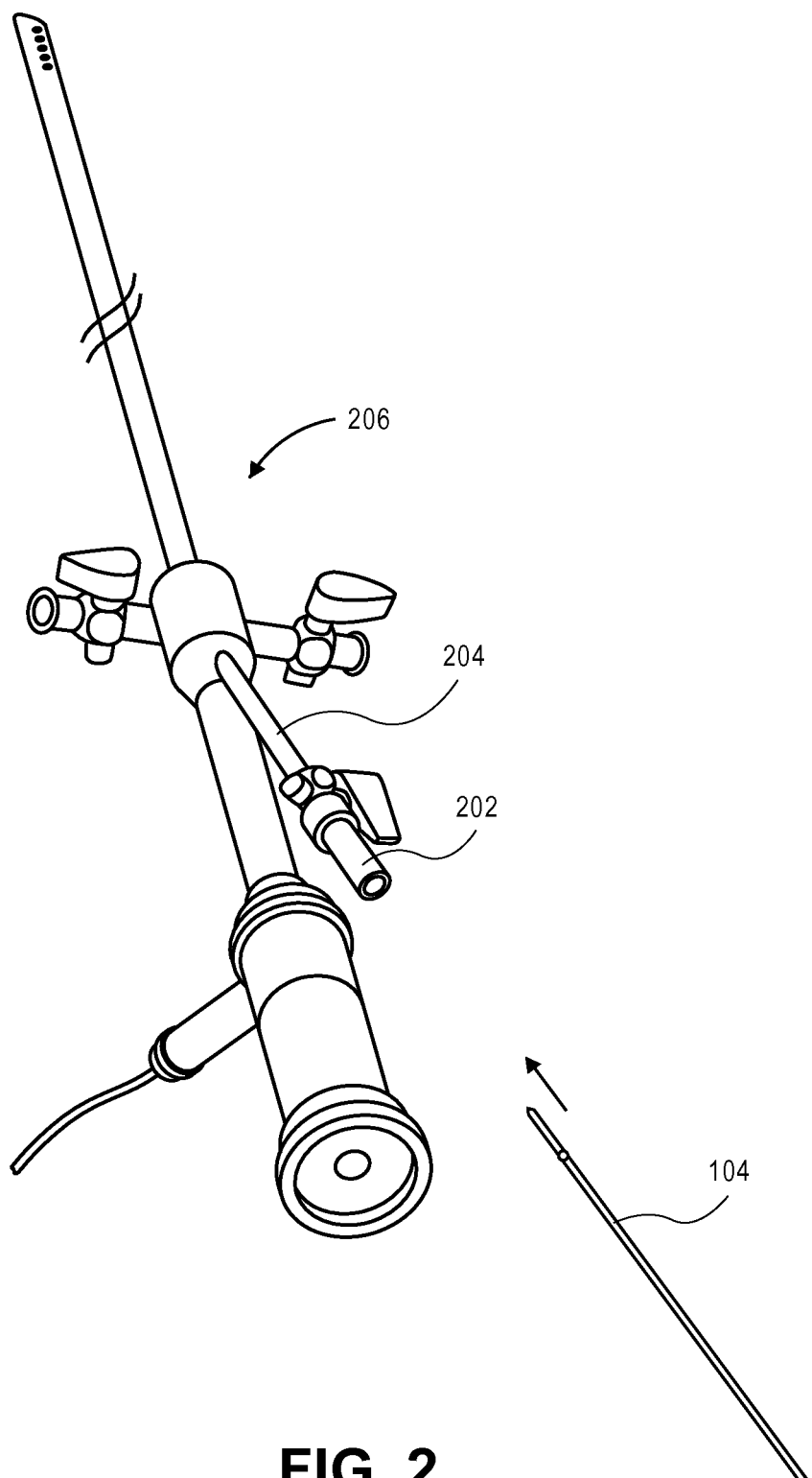
FIG. 2 is an illustration of a delivery catheter of a delivery system before insertion into an endoscope.
Figure 3:
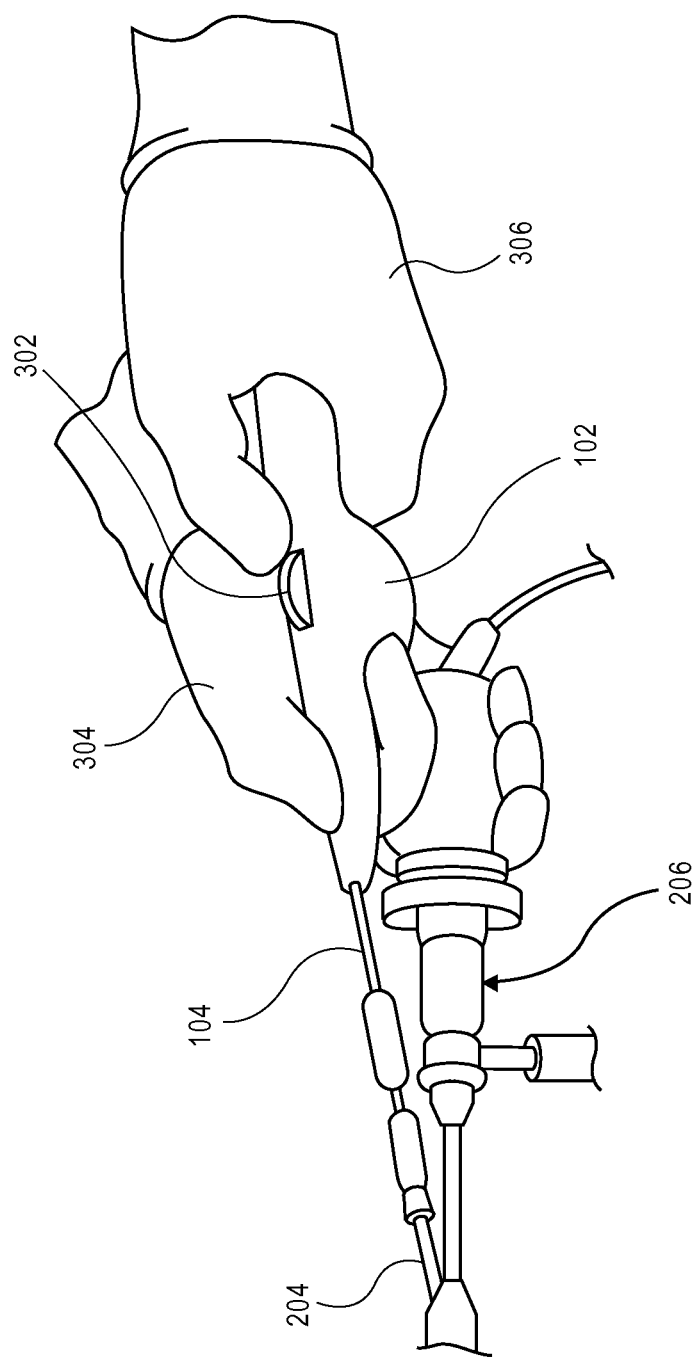
FIG. 3 is an illustration of a physician deploying a contraceptive implant according to an instruction for use.
Figure 4:
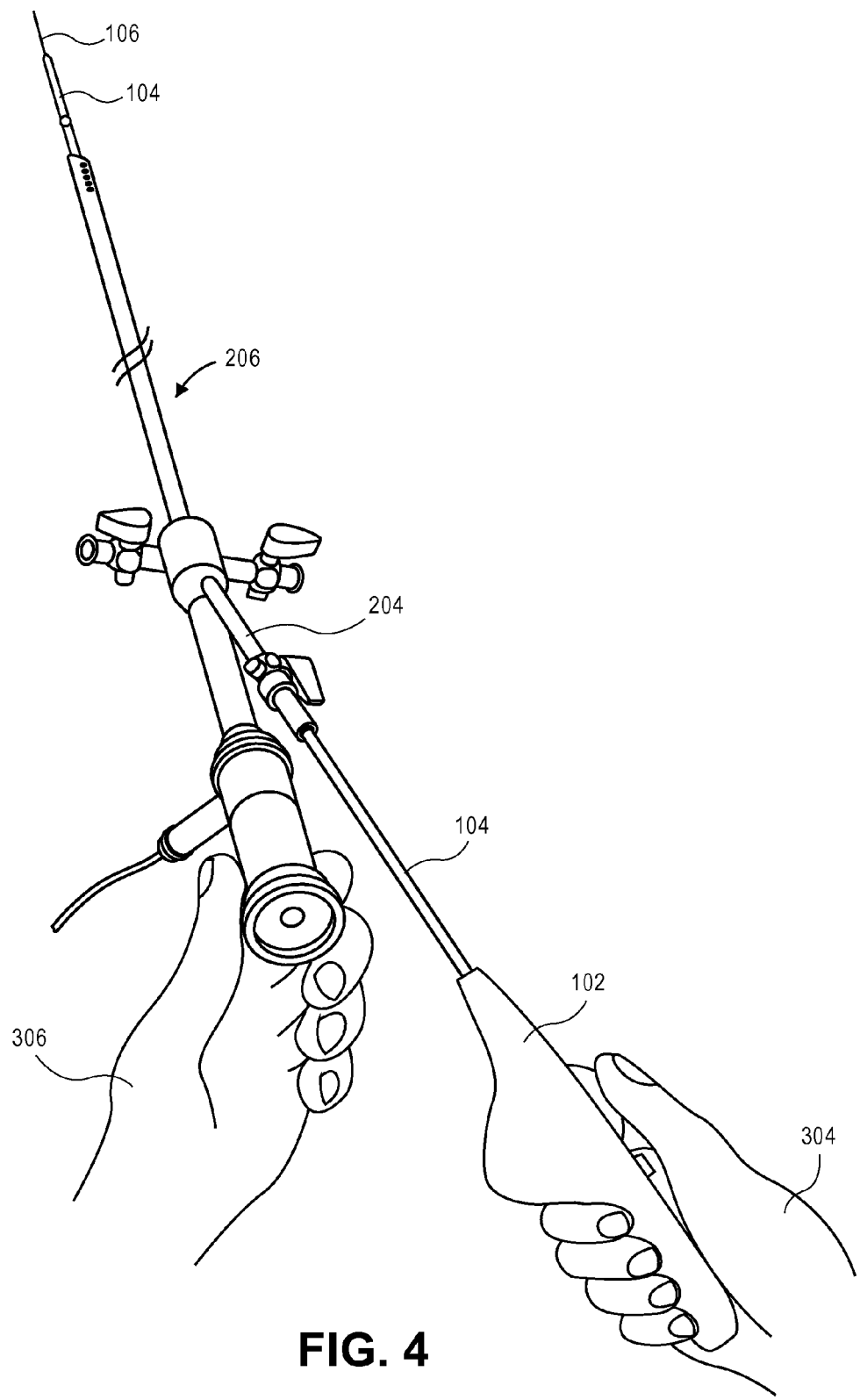
FIG. 4 is an illustration of a physician improperly deploying a contraceptive implant contrary to an instruction for use.

Embodiments of the invention describe systems and methods for use in minimally invasive gynecological procedures, such as methods of preventing pregnancy by inserting intrafallopian contraceptive devices into the fallopian tubes. Referring to FIG. 4, an illustration of a physician deploying a contraceptive implant contrary to an instruction for use is shown. In practice, rather than follow the aforementioned instructions, a physician may grasp handle assembly 102 with first hand 304 and endoscope 206 with second hand 306 while positioning delivery catheter 104 and deploying the insert. This technique can cause delivery catheter 104 to move relative to endoscope 206, as well as move relative to the fallopian tube, during deployment. Such relative movement may have an undesirable consequence of inaccurately positioning and deploying the insert in the fallopian tube, since delivery catheter 104 may shift during deployment.

In an aspect, a handle assembly of a delivery system includes deployment mechanisms and features that facilitate stabilization of the handle assembly against an endoscope, e.g., a hysteroscope, during deployment of an occlusion device insert. This may be accomplished by incentivizing physicians to use two hands to actuate the handle assembly. In an embodiment, physicians may be incentivized to use two hands by making it easier to actuate the handle assembly with two hands, as compared to using only one hand. For example, actuation of the handle assembly to deploy an occlusion device insert may require movement of a proximal handle relative to a distal handle through a first travel to withdraw a catheter sheath and through a second travel to withdraw a delivery wire. Movement through both travels may urge or require a physician to use both hands since the range of motion through both travels may be greater than the range of motion that can be ergonomically produced using one hand. In an embodiment, the use of two hands stabilizes the handle assembly against the endoscope, producing minimal relative movement between a delivery catheter of the delivery system and the endoscope. The minimal relative movement facilitates accurate placement of the occlusion device within the target anatomy.

In another aspect, a handle assembly of a delivery system includes a sleeve mechanism that facilitates repositioning of the handle assembly relative to an endoscope without having to release the endoscope. In an embodiment, the sleeve slides over a portion of the handle assembly and moves from a gripping configuration when squeezed tightly, to a sliding configuration when squeezed lightly. Thus, a physician may continue to grip the endoscope and the sleeve in one hand while repositioning the handle assembly, which may be gripped by another hand.

It is to be understood that embodiments of the current invention may be used for gynecological, as well as non-gynecological, minimally invasive surgeries and target anatomies. For example, relevant surgeries include those that employ endoscopes, such as angioscopy, arthroscopy, bronchoscopy, and hysteroscopy, to name a few. However, many target anatomies may benefit from such procedures, including gynecological anatomies such as the fallopian tubes, and non-gynecological target anatomies, such as the vas deferens, e.g., during a male sterilization procedure, or arteries, e.g., during a vascular intervention.

Figure 5:
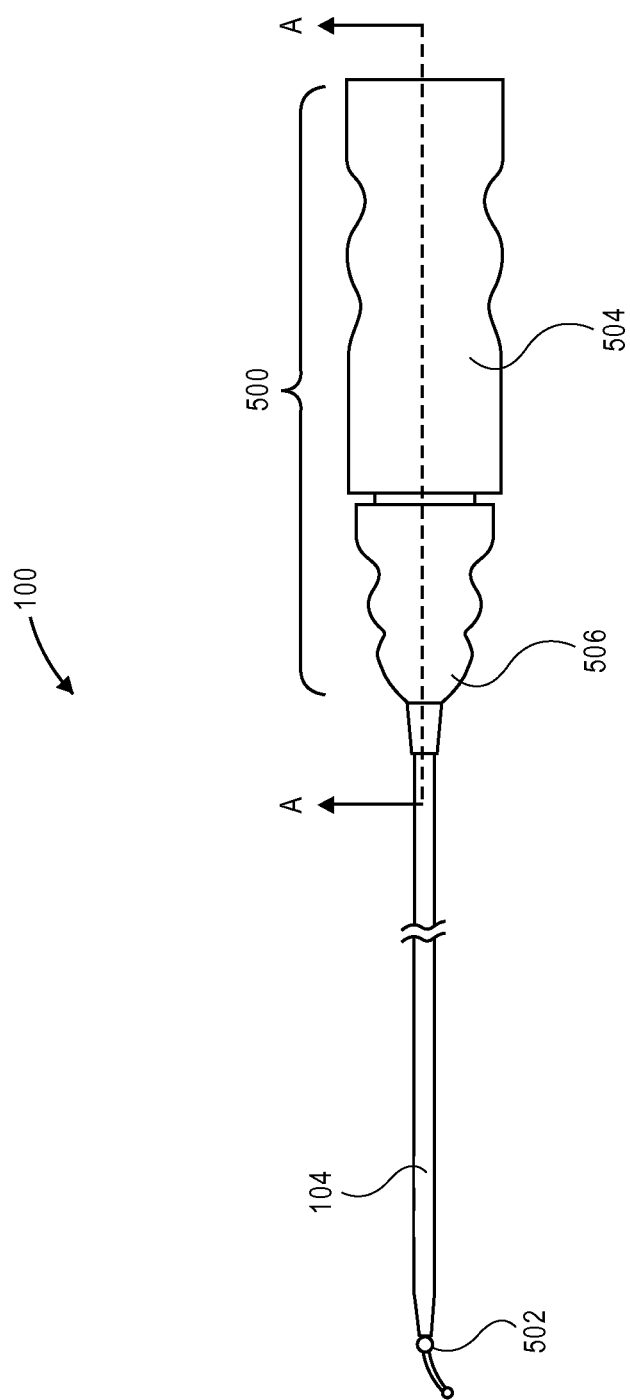
FIG. 5 is a side view of a delivery system having a handle assembly with a distal handle and a proximal handle in accordance with an embodiment of the invention.

Referring to FIG. 5, a side view of a delivery system having a handle assembly with a distal handle and a proximal handle is shown in accordance with an embodiment of the invention. Delivery system 100 may include a delivery catheter 104 coupled with a handle assembly 500. Handle assembly 500 may be used to position delivery catheter 104 within a fallopian tube by moving delivery catheter 104 within working channel 204 of endoscope 206. Furthermore, handle assembly 500 may be actuated to deploy an occlusion device 502 from within delivery catheter 104 into a fallopian tube. For example, a proximal handle 504 may be moved relative to a distal handle 506 to retract outer sheath 508 over occlusion device 502, exposing occlusion device 502 for deposition within the fallopian tube.

In an embodiment, the occlusion device 502 may be a contraceptive device that provides permanent contraception or sterilization. Examples of contraceptive devices and methods for using these devices with delivery systems are provided in U.S. Pat. No. 6,705,323, U.S. Pat. No. 6,709,677, U.S. Pat. No. 8,360,064, and U.S. patent application Ser. No. 12/605,304.

Figure 6A:
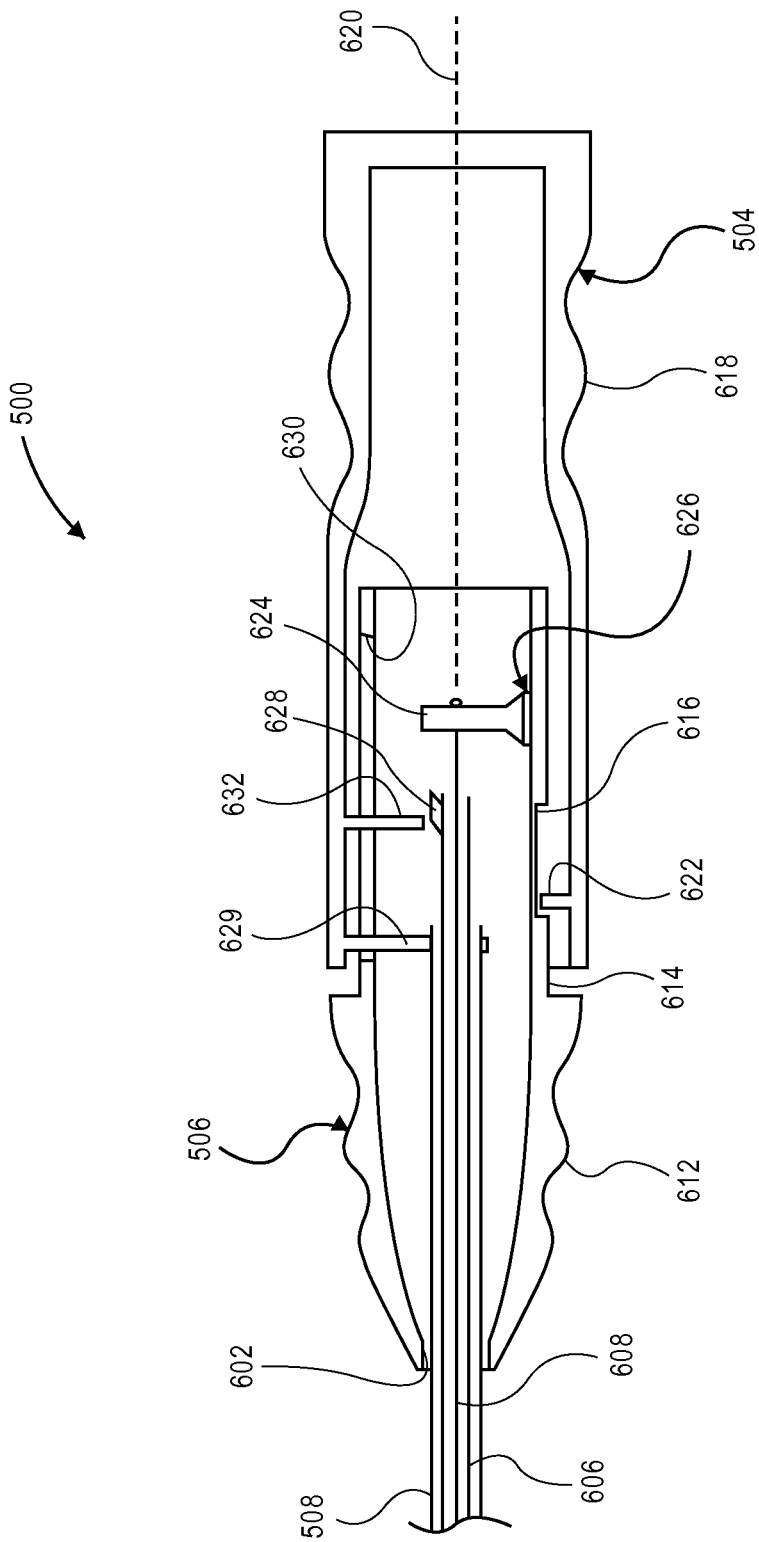
FIG. 6A is a cross-sectional view, taken about line A-A of FIG. 5, of a delivery system having a proximal handle in an initial position relative to a distal handle in accordance with an embodiment of the invention.

Referring to FIG. 6A, a cross-sectional view, taken about line A-A of FIG. 5, of a delivery system having a proximal handle in an initial position relative to a distal handle is shown in accordance with an embodiment of the invention. Distal handle 506 includes a nose port 602 to receive delivery catheter 104. In an embodiment, delivery catheter 104 includes an outer sheath 508 encompassing an inner catheter 606 and a delivery wire 608. Delivery catheter 104 may insert through nose port 602 such that it is supported by handle assembly 500. Handle assembly 500 may include a strain relief (not shown) around outer sheath 508 near nose port 602 to prevent kinking of delivery catheter 104.

In an embodiment, distal handle 506 may include a distal grip 612 for a physician to grasp. Distal grip 612 may include, for example, a knurled, roughened, or wavy surface that can be held. For example, distal grip 612 may include one or more concave reliefs that curve inward from a surface of distal grip 612 and accommodate the fingertips of a physician. Distal handle 506 may also include a shaft 614 protruding from distal handle 506. Shaft 614 may include an outer surface, which in an embodiment, is generally cylindrical. The outer surface of shaft 614 may also include one or more channel 616. Channel 616 may be formed entirely through a wall thickness of shaft 614, or it may be a blind recess extending through only a portion of the wall thickness, as shown. In an embodiment, channel 616 defines a path, or travel, extending some distance over shaft 614.

In an embodiment, proximal handle 504 may include a proximal grip 618 for a physician to grasp. Proximal grip 618 may include, for example, a knurled, roughened, or wavy surface that can be held. For example, proximal grip 618 may include one or more concave reliefs that curve inward from a surface of proximal grip 618 and accommodate the fingertips of a physician. In an embodiment, proximal handle 504 may have an inner surface that conforms to the outer surface of shaft 614, and therefore allows proximal grip 618 to slide over shaft 614. For example, inner surface of proximal handle 504 may be generally cylindrical to conform to the shape of shaft 614 outer surface. Furthermore, distal handle 506 and proximal handle 504 may be coaxially arranged along an axis 620.

Proximal handle 504 may include a nib 622 projecting from the inner surface to engage channel 616 formed within the outer surface of shaft 614. Nib 622 and channel 616 may be operably joined in a manner that constrains the free movement of nib 622 to a path defined by channel 616. For example, at least a portion of channel 616 may be aligned with axis 620, as shown. Nib 622 may be located within channel 616 to allow proximal handle 504 to be pulled relative to distal handle 506, but to disallow proximal handle 504 to rotate relative to distal handle 506 within the axially arranged segment of channel 616. Thus, proximal handle 504 may move relative to distal handle 506 in a manner defined by the path of channel 616 over which nib 622 translates.

In an embodiment, handle assembly 500 may further include a delivery wire mount 624 operably joined with distal handle 506 and capable of moving relative to distal handle 506. For example, delivery wire mount 624 may abut against an inner surface of shaft 614 and slide relative to the inner surface on a mount slide 626. In an embodiment, mount slide 626 provides a bearing surface between delivery wire mount 624 and shaft 614 inner surface, and furthermore includes a connecting feature. For example, mount slide 626 may include a dovetail slide (not shown) having a v-shaped groove formed in either delivery wire mount 624 or the inner surface of shaft 614 to receive a protruding dovetail feature on an opposing surface. Thus, in an embodiment, an axial load applied to delivery wire mount 624 causes delivery wire mount 624 to slide relative to distal handle 506.

Distal handle 506, proximal handle 504, and delivery wire mount 624 may be operably associated with one or more delivery catheter 104 components. For example, proximal handle 504 may include an outer sheath mount 629 projecting from an inner surface to hold a proximal portion of outer sheath 508. In an embodiment, outer sheath mount 629 may project through a first shaft window 630 formed through a wall thickness of shaft 614. Thus, outer sheath mount 629 may fix the axial position of outer sheath 508 relative to proximal handle 504 even when shaft 614 separates those components. In an embodiment, outer sheath mount 629 may be affixed to outer sheath 508 by an adhesive or thermal bond.

In an embodiment, distal handle 506 may include an inner catheter mount 628 anchoring inner catheter 606 to an inner surface of distal handle 506. For example, inner catheter mount 628 may project from an inner surface of distal handle 506 and may be affixed to inner catheter 606 using an adhesive or thermal bond.

In an embodiment, delivery wire mount 624 may hold delivery wire 608. However, delivery wire mount 624 may be operably associated with either distal handle 506 or proximal handle 504. More specifically, delivery wire mount 624 may remain stationary relative to distal handle 506 when no external force is exerted upon it. However, when biased by an external load, delivery wire mount 624 may slide relative to distal handle 506, and thus, delivery wire mount 624 may become operably coupled with a body providing the external load. For example, proximal handle 504 may include an arm 632 projecting through first shaft window 630 into a region within distal handle 506. A distal end of arm 632 may further be axially aligned with delivery wire mount 624, such that movement of arm 632 can cause arm 632 to contact delivery wire mount 624. In this way, arm 632 can exert a load on delivery wire mount 624. Accordingly, the instantaneous configuration of handle assembly 500 determines whether delivery wire mount 624 is operably coupled with distal handle 506 and proximal handle 504.

Figure 6B:
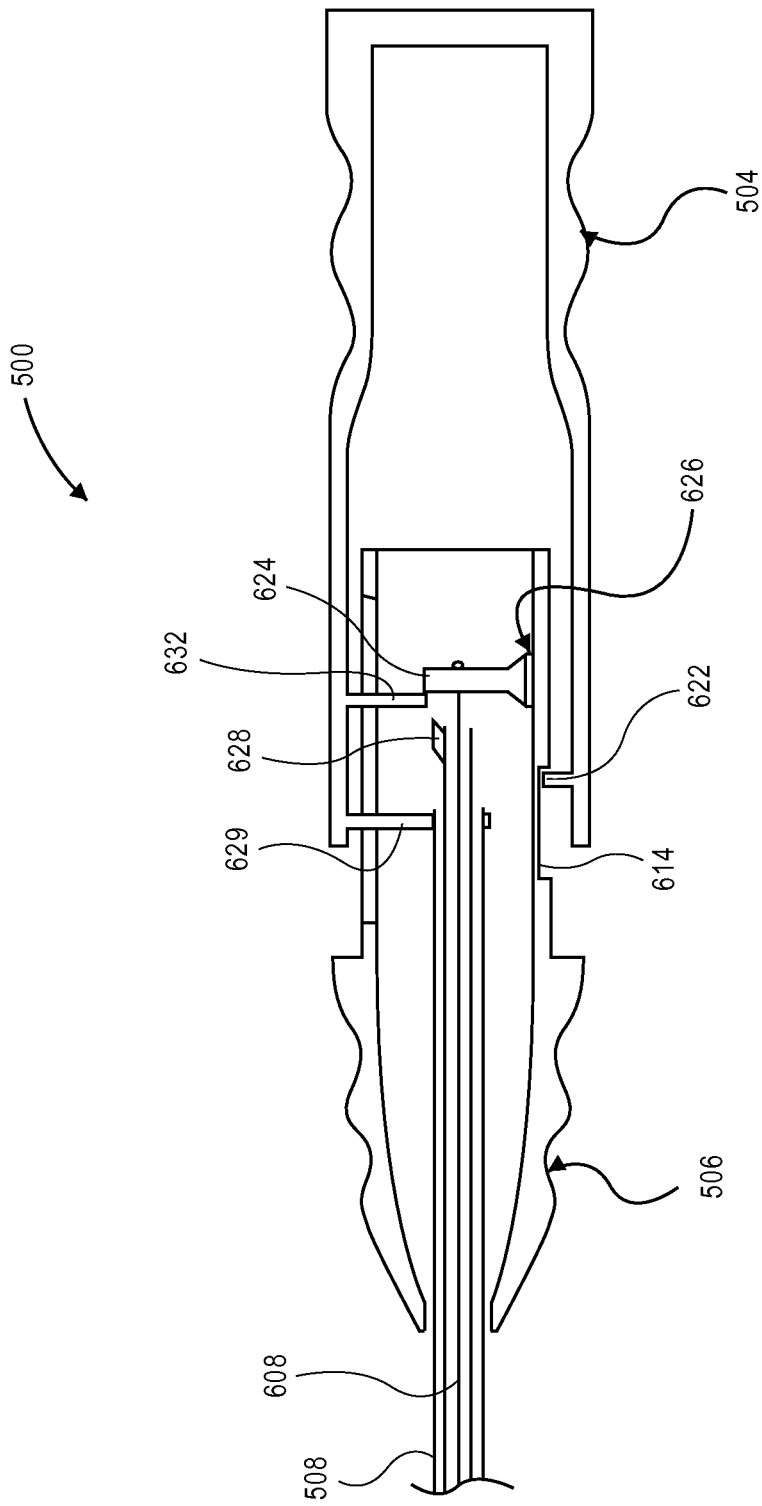
FIG. 6B is a cross-sectional view, taken about line A-A of FIG. 5, of a delivery system having a proximal handle moved through a first travel relative to a distal handle in accordance with an embodiment of the invention.
Figure 7A:
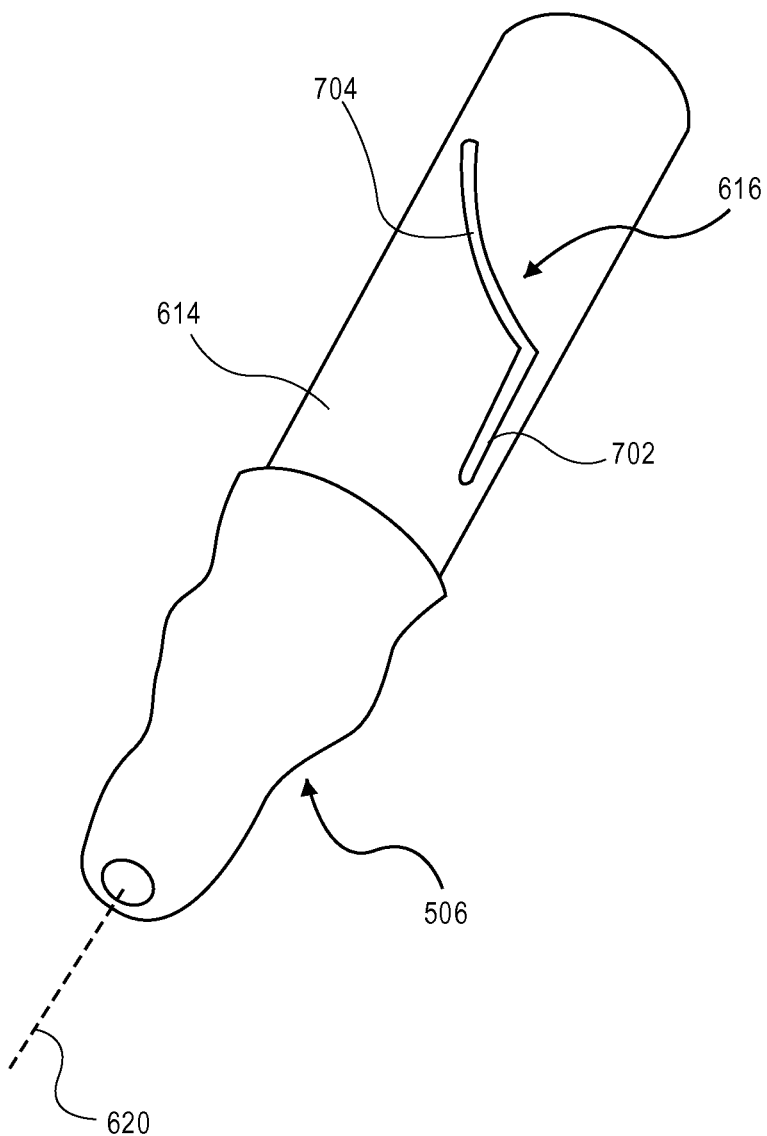
FIG. 7A is a perspective view of a distal handle having a channel with a first travel and a second travel in accordance with an embodiment of the invention.

Referring to FIG. 6B, a cross-sectional view, taken about line A-A of FIG. 5, of a delivery system having a distal handle moved through a first travel relative to a proximal handle is shown in accordance with an embodiment of the invention. Here, proximal handle 504 has been moved relative to distal handle 506, e.g., by pulling proximal handle 504 with one hand while stabilizing distal handle 506 with another hand. The relative movement may be defined by the movement of nib 622 within channel 616. For example, as distal handle 506 is pulled, nib 622 may move from a distal end of the illustrated channel 616 portion to a proximal end of the channel 616 portion. This portion of channel 616 may not represent the entire path of channel 616, i.e., it may only be a first travel (FIG. 7A). In an embodiment, movement of proximal handle 504 relative to distal handle 506 through the first travel retracts outer sheath 508 over inner catheter 606, and may also bring arm 632 into contact with delivery wire mount 624 fixed to delivery wire 608.

Accordingly, in an embodiment, during movement of proximal handle 504 through first travel, handle assembly 500 may be configured such that outer sheath 508 is operably coupled with proximal handle 504 through outer sheath mount 629, inner catheter 606 is operably coupled with distal handle 506 through inner catheter mount 628, and delivery wire mount 624 is operably coupled with distal handle 506 through mount slide 626. These relationships may change as handle assembly 500 is actuated further, as described below.

Figure 6C:
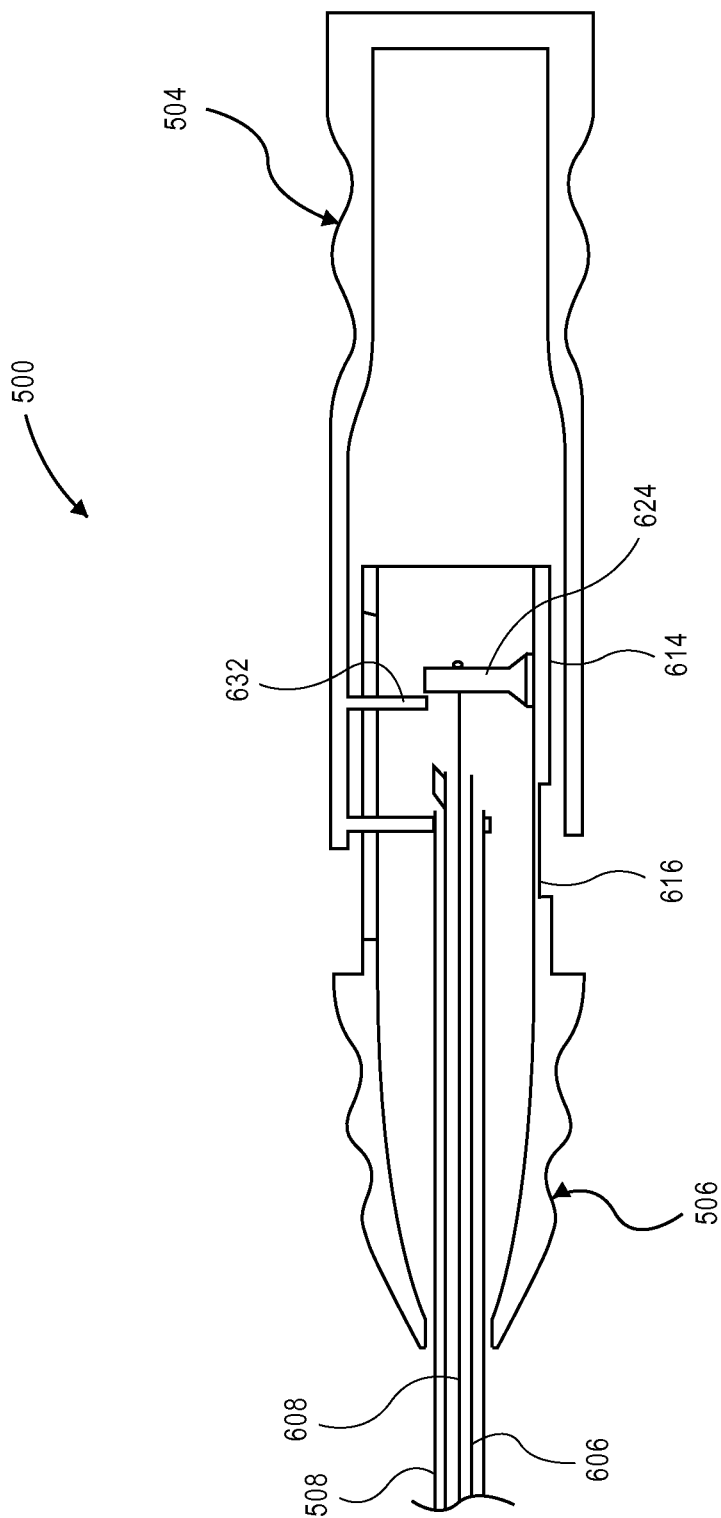
FIG. 6C is a cross-sectional view, taken about line A-A of FIG. 5, of a delivery system having a proximal handle moved through a second travel relative to a distal handle in accordance with an embodiment of the invention.

Referring to FIG. 6C, a cross-sectional view, taken about line A-A of FIG. 5, of a delivery system having a proximal handle moved through a second travel relative to a distal handle is shown in accordance with an embodiment of the invention. Here, proximal handle 504 has continued to move relative to distal handle 506, e.g., by rotating proximal handle 504 with one hand while stabilizing distal handle 506 with another hand. The additional movement may be defined by movement of nib 622 within channel 616, and more specifically, within a different portion of channel 616 from that shown formed in an outer wall of shaft 614. In an embodiment, the different portion may define a second travel (FIG. 7A). In an embodiment, movement of proximal handle 504 relative to distal handle 506 through the second travel continues to retract outer sheath 508, which remains anchored to proximal handle by outer sheath mount 629, while inner catheter 606, which is anchored by inner catheter mount 628, remains stationary relative to distal handle 506. In addition, arm 632 may exert a load on delivery wire mount 624 over the second travel, causing delivery wire mount 624 to slide proximally over a mating surface of shaft 614, and therefore move relative to distal handle 506 while remaining positionally fixed relative to proximal handle 504.

Accordingly, in an embodiment, during movement of proximal handle 504 through second travel, handle assembly 500 may be configured such that outer sheath 508 is operably coupled with proximal handle 504 through outer sheath mount 629, inner catheter 606 is operably coupled with distal handle 506 through inner catheter mount 628, and delivery wire mount 624 is operably coupled proximal handle 504 through arm 632.

Figure 6D:
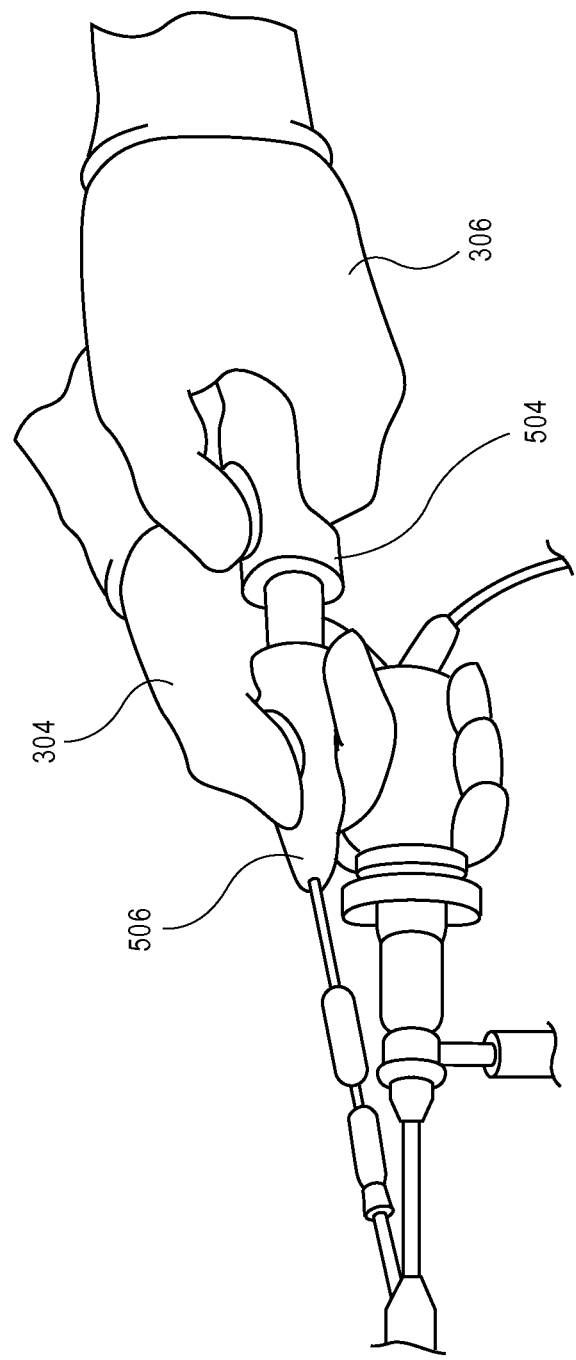
FIG. 6D is an illustration of a physician actuating a handle assembly in accordance with an embodiment of the invention.

Referring to FIG. 6D, an illustration of a physician actuating a handle assembly in accordance with an embodiment of the invention is shown. Given the distance and relative motion that accompanies movement between distal handle 506 and proximal handle 504 during actuation of handle assembly 500 through the first travel and the second travel, a physician using handle assembly 500 to deploy occlusion device 502 may find it difficult to perform the actuation with only one hand. For example, a physician may find it difficult or impossible to grasp the distal handle 506 between thumb and forefinger of one hand while grasping the proximal handle 504 between palm and little finger of the same hand, and still generate sufficient range of motion between distal handle 506 and proximal handle 504 to traverse the entire path of channel 616. Accordingly, the illustrated design incentivizes, if not requires, the physician to use two hands to actuate handle assembly 500, since doing so may be substantially easier than using only one hand.

Referring to FIG. 7A, a perspective view of a distal handle having a channel with a first travel and a second travel is shown in accordance with an embodiment of the invention. The range of motion of channel 616 includes first travel 702 and second travel 704. In an embodiment, first travel 702 is axially oriented within shaft 614 and second travel 704 is rotationally oriented within shaft 614, relative to axis 620. As a result, nib 622 may be slid through first travel 702 by pulling on proximal handle 504 with one hand while stabilizing distal handle 506 against endoscope 206 with another hand. Furthermore, nib 622 may be slid through second travel 704 by twisting proximal handle 504 with one hand while stabilizing distal handle 506 with another hand. In an embodiment, second travel 704 may have a corkscrew pattern traversing one or more rotations about shaft 614. Therefore, twisting of proximal handle 504 through second travel 704 may be difficult to achieve without the use of two hands.

Figure 7B:
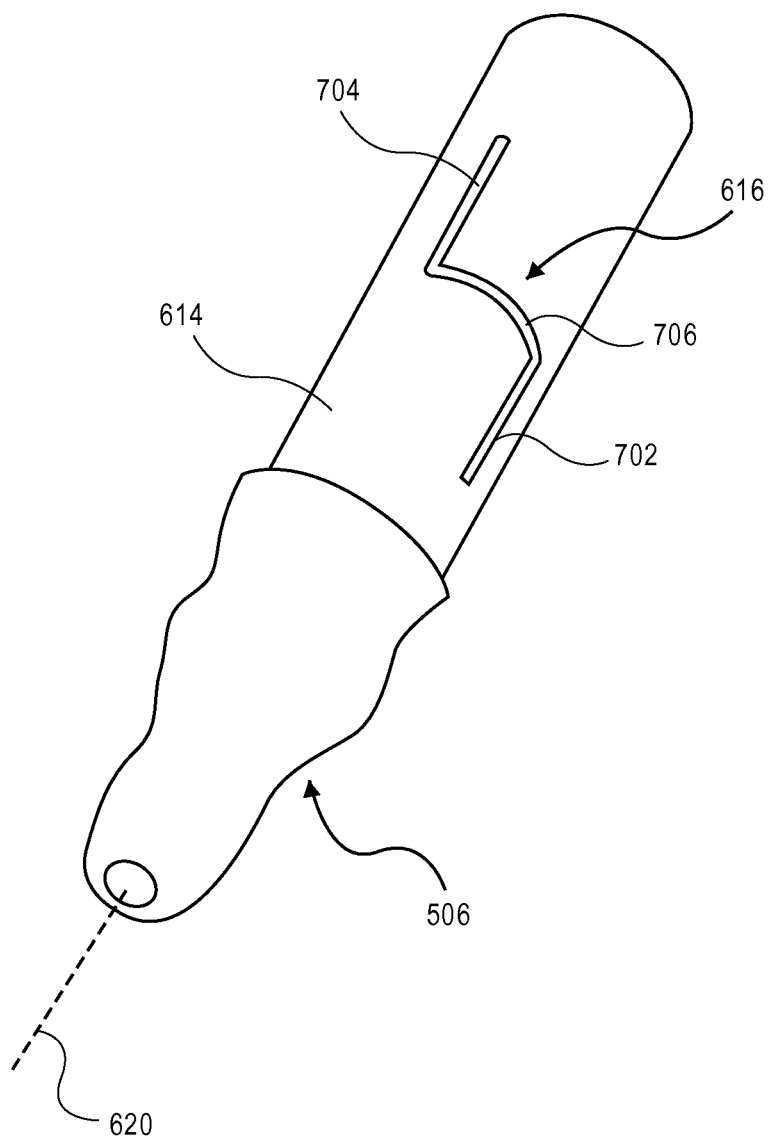
FIG. 7B is a perspective view of a distal handle having a channel with a first travel, an intermediate travel, and a second travel in accordance with an embodiment of the invention.

Referring to FIG. 7B, a perspective view of a distal handle having a channel with a first travel, an intermediate travel, and a second travel is shown in accordance with an embodiment of the invention. The range of motion of channel 616 includes first travel 702, second travel 704, and an intermediate travel 706 therebetween. In an embodiment, both first travel 702 and second travel 704 are axially oriented, while intermediate travel 706 is circumferentially oriented. That is, to traverse first travel 702 and second travel 704, a physician may pull proximal handle 504 with one hand while stabilizing distal handle 506 with another hand. However, between first travel 702 and second travel 704, the physician is required to twist proximal handle 504 in a clockwise fashion to move nib 622 from the proximal end of first travel 702 of channel 616 to the distal beginning of second travel 704 of channel 616. Therefore, the overall length of channel 616 and the various pulling and twisting motions required to traverse the length may be difficult to achieve without the use of two hands.

In another embodiment, channel 616 may be formed in an inner surface of proximal handle 504 and nib 622 may be formed on an outer surface distal handle 506. Thus, the configurations of first travel 702, intermediate travel 706, and second travel 704 described above are illustrative and not restrictive. For example, in an embodiment, distal handle 506 and proximal handle 504 may include threaded surfaces that are screwed together and one or more travel lengths may be defined by the rotation of distal handle 506 and proximal handle 504 relative to each other using the threads.

Figure 8:
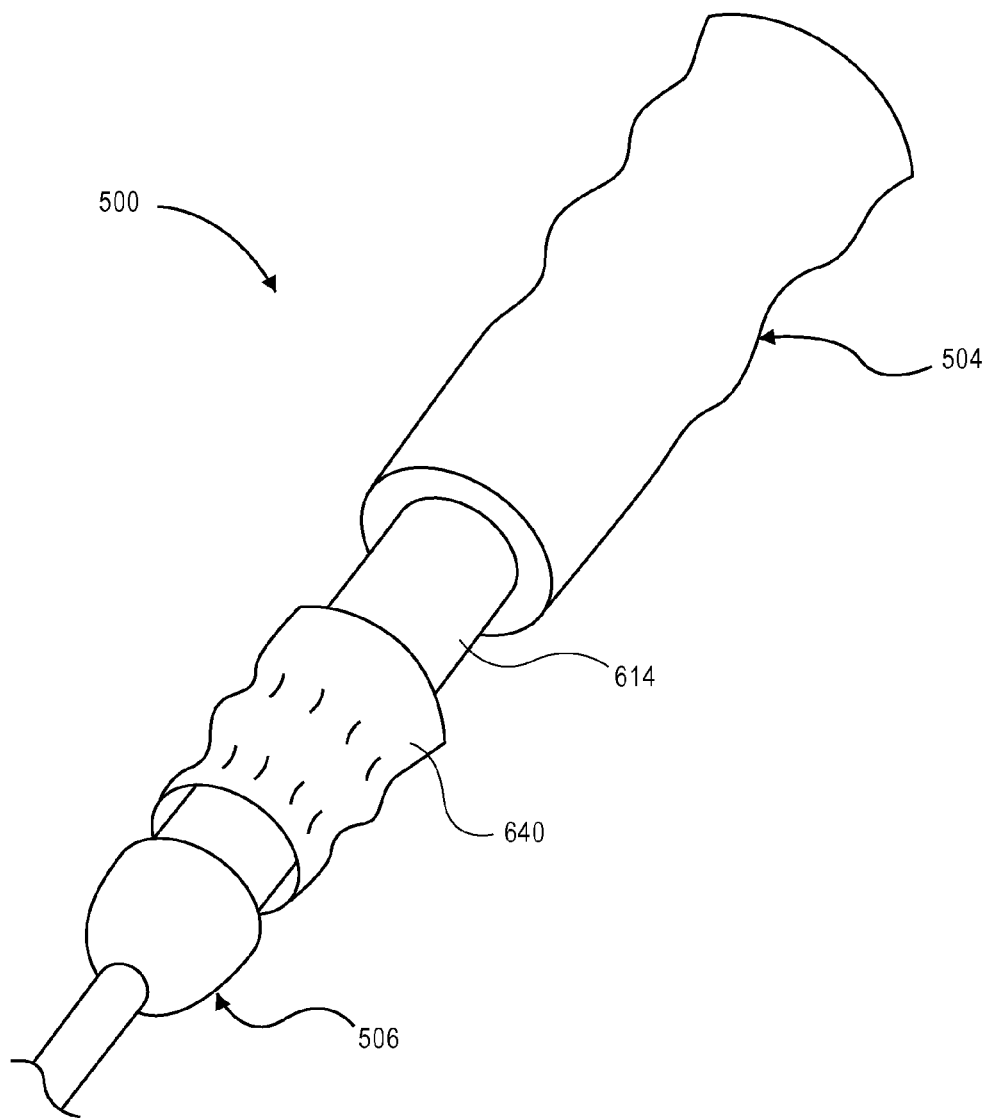
FIG. 8 is a perspective view of a handle assembly having a sleeve over a handle shaft in accordance with an embodiment of the invention.

Referring to FIG. 8, a perspective view of a handle assembly having a sleeve over a handle shaft is shown in accordance with an embodiment of the invention. A sleeve 640 located over and/or around shaft 614 of distal handle 506 may be useful in allowing a physician to intermittently grip or release distal handle 506 depending on the pressure applied to sleeve 640. This intermittent action allows the physician to either actuate handle assembly 500 when gripping sleeve 640 tightly, or to reposition handle assembly relative to sleeve 640 when gripping sleeve 640 lightly. More specifically, sleeve 640 may be squeezed tightly to grip distal handle 506, allowing distal handle 506 to be moved separately from proximal handle 504. Alternatively, sleeve 640 may be able to slide over shaft 614, such that moving proximal handle 504 with one hand while squeezing sleeve 640 lightly with another hand may allow shaft 614 to slide through sleeve 640. Thus, in an embodiment, when first hand 304 grasps sleeve 640 and second hand 306 grasps proximal handle 504, pulling or pushing on proximal handle 504 while stabilizing sleeve 640 will result in distal handle 506 and proximal handle 504 both moving together relative to sleeve 640.

Figure 9A:
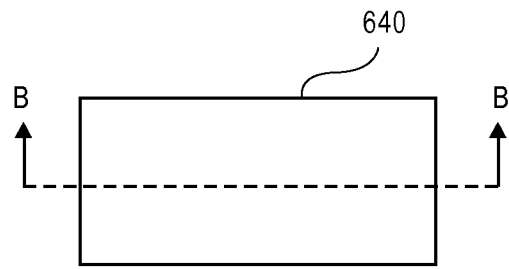
FIG. 9A is a side view of a sleeve in accordance with an embodiment of the invention.
Figure 9B:
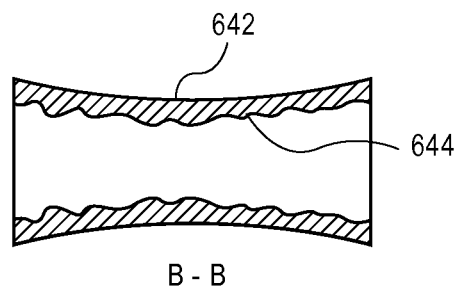
FIG. 9B is a cross-sectional view, taken about line B-B of FIG. 9A, of a sleeve in accordance with an embodiment of the invention.

Referring to FIG. 9A, a side view of a sleeve is shown in accordance with an embodiment of the invention. In an embodiment, sleeve 640 includes a generally cylindrical form with a length, an outer diameter, and an inner diameter. Referring to FIG. 9B, a cross-sectional view, taken about line B-B of FIG. 9A, of a sleeve is shown in accordance with an embodiment of the invention. In an embodiment, sleeve 640 includes a flexible element 642. Flexible element 642 may be configured in numerous manners to allow flexible element 642 to flex toward the inner diameter of sleeve 640 when squeezed. For example, sleeve 640 may be formed from a flexible and resilient material such as silicone, allowing flexible element 642 to deform inward when squeezed and to spring outward to an original condition when released. Alternative materials may be used to form flexible element 642, such as polyether block amides or other thermoplastic elastomers. In addition, sleeve 640 may be dimensioned such that flexible element 642 is more flexible, e.g., thinner, than other portions of sleeve 640 to facilitate the springing function described above.

In an embodiment, sleeve 640 may include an inner grip 644 to grip shaft 614 when sleeve 640 is squeezed. For example, inner grip 644 may include a knurled, roughened, or wavy surface, or otherwise include features that resist motion of shaft 614 within sleeve 640 when sleeve 640 is squeezed. Furthermore, inner grip 644 may be surface treated, e.g., with a pressure-sensitive adhesive sprayed or coated on the inner diameter of sleeve 640, to improve tackiness and grip on shaft 614 when sleeve 640 is squeezed.

Figure 10A:
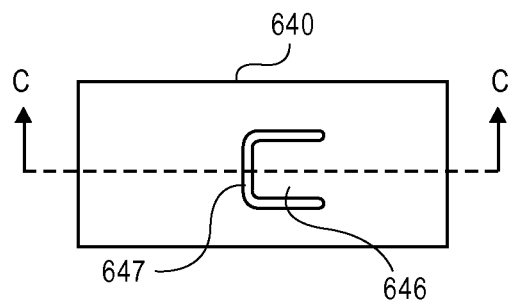
FIG. 10A is a side view of a sleeve in accordance with an embodiment of the invention.
Figure 10B:
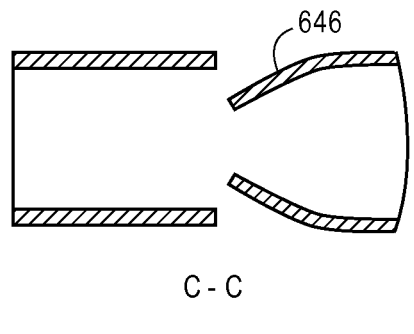
FIG. 10B is a cross-sectional view, taken about line C-C of FIG. 10A, of a sleeve in accordance with an embodiment of the invention.

Referring to FIG. 10A, a side view of a sleeve is shown in accordance with an embodiment of the invention. In an embodiment, flexible element 642 of sleeve 640 may include one or more tab 646. For example, tab 646 may be formed by laser cutting or micro-machining a tab outline 648 through a wall thickness of sleeve 640, thereby creating tab 646 from sleeve 640. Referring to FIG. 10B, a cross-sectional view, taken about line C-C of FIG. 10A, of a sleeve is shown in accordance with an embodiment of the invention. Tab 646 may be squeezed inward to press against shaft 614 within sleeve 640. As first and second tab 646 on radially offset locations of sleeve 640 are squeezed, the tabs tend to angle inward such that the edge of tab 646 grips shaft 614 and resists motion, particularly in a direction opposite to the tab 646 angle.

Figure 11A:
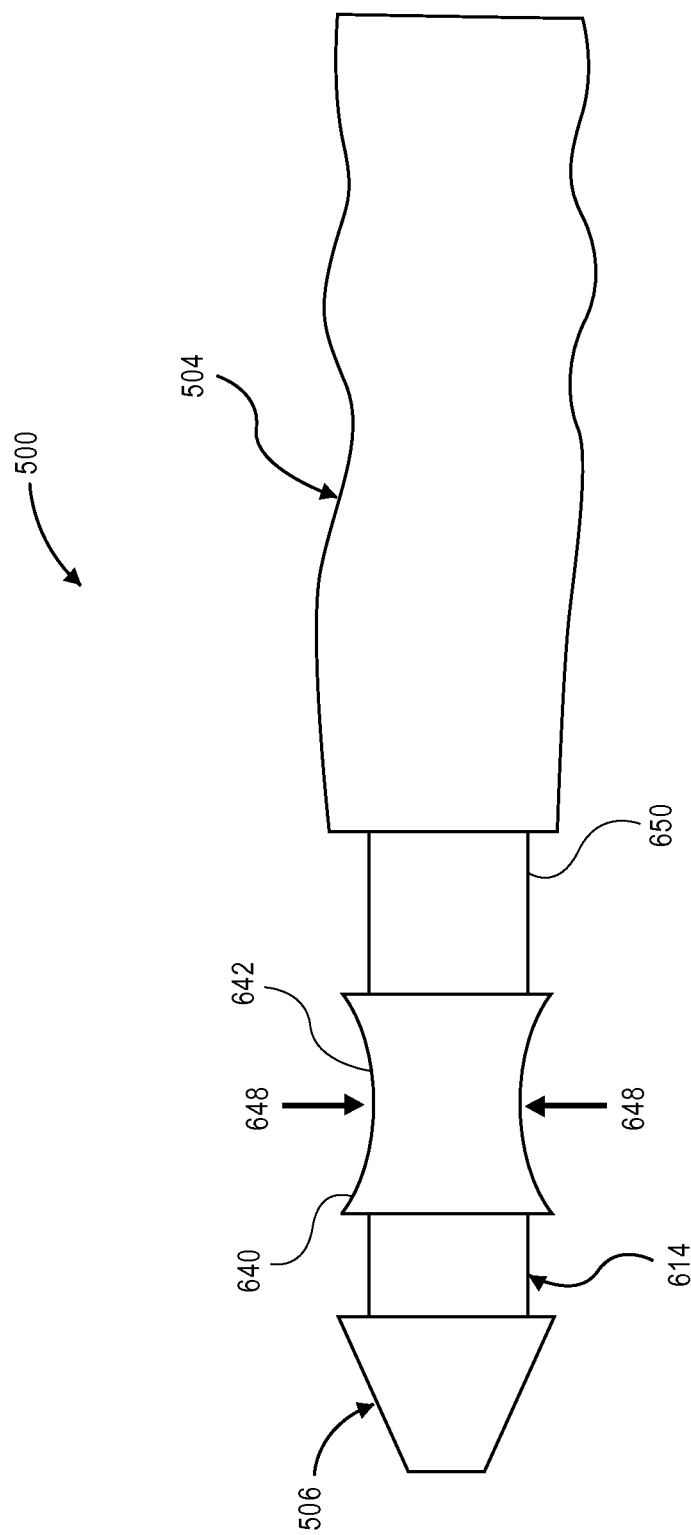
FIG. 11A is a side view of a handle assembly having a sleeve during deployment of an occlusion device in a fallopian tube in accordance with an embodiment of the invention.

Referring to FIG. 11A, a side view of a handle assembly having a sleeve during deployment of an occlusion device in a fallopian tube is shown in accordance with an embodiment of the invention. In an embodiment, a lateral load, e.g., squeeze 648, is applied to sleeve 640 by a physician to cause flexible element 642 to bias inward toward, and grip onto, a gripping surface 650 of shaft 614. While sleeve 640 grips shaft 614, a physician may move proximal handle 504 relative to distal handle 506, e.g., by pulling or twisting proximal handle 504 through first travel 702 or second travel 704. Thus, in an embodiment, a physician can squeeze sleeve 640 and stabilize distal handle 506 against endoscope 206 with one hand while pulling on proximal handle 504 with another hand to actuate handle assembly 500.

Figure 11B:
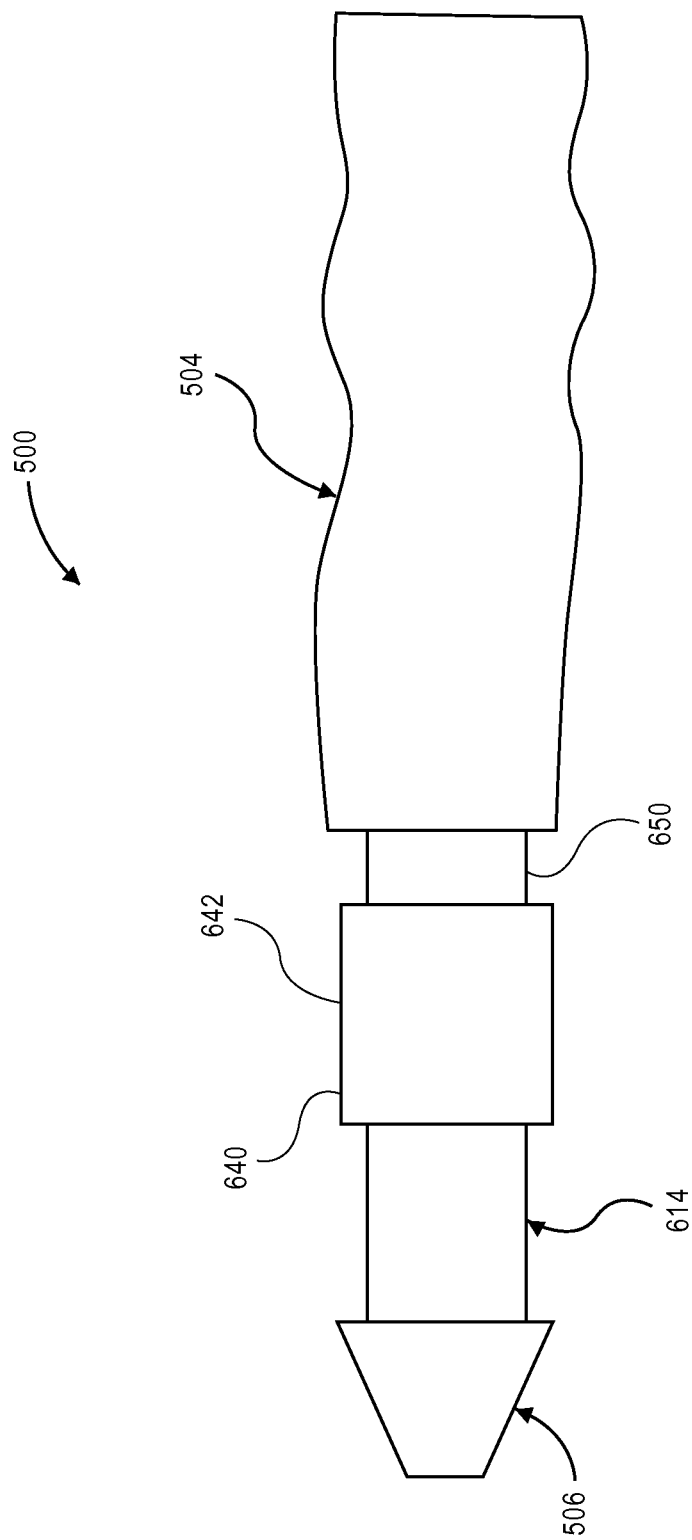
FIG. 11B is a side view of a handle assembly having a sleeve during repositioning of an occlusion device in a fallopian tube in accordance with an embodiment of the invention.

Referring to FIG. 11B, a side view of a handle assembly having a sleeve during repositioning of an occlusion device in a fallopian tube is shown in accordance with an embodiment of the invention. In an embodiment, the physician releases squeeze 648 from sleeve 640, such that flexible element 642 rebounds to an initial configuration in which inner grip 644 does not contact gripping surface 650. While sleeve 640 is released from shaft 614, a physician may move proximal handle 504 and distal handle 506 in unison with one hand. That is, a physician can stabilize sleeve 640 against endoscope 206 with one hand while moving proximal handle 504 with another hand. As a result, distal handle 506 can slide through sleeve 640 to a new location. This technique may be used to reposition delivery catheter 104 within fallopian tube 1304, e.g., between actuation of handle assembly 500 through first travel 702 and second travel 704.

Figure 12:
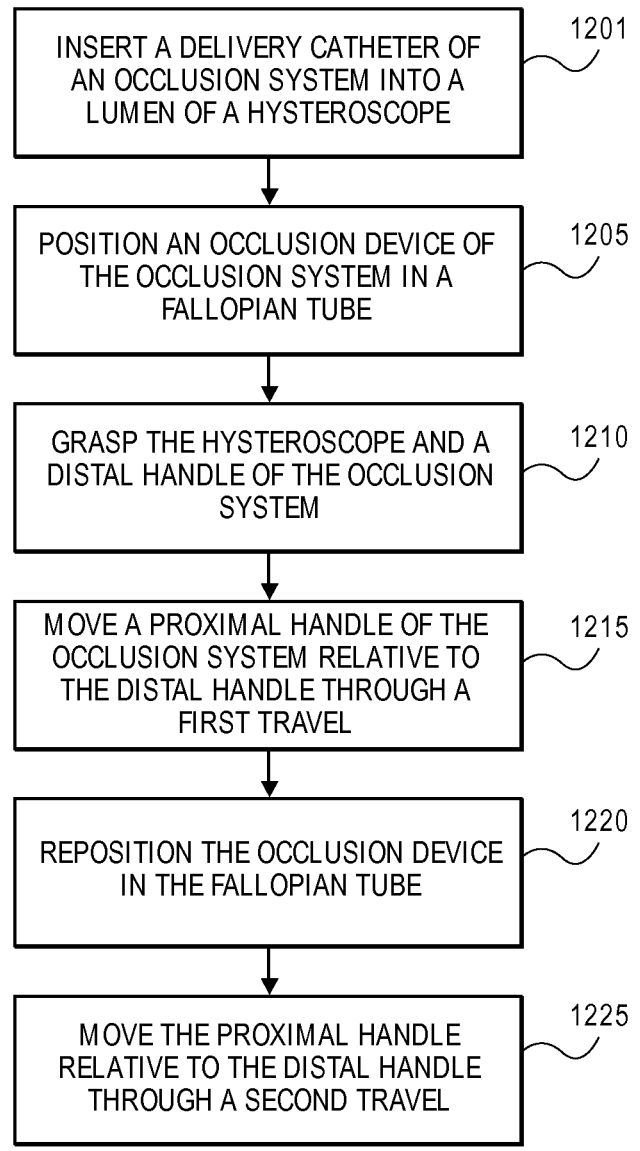
FIG. 12 is a flowchart of a method for deploying an occlusion device in a fallopian tube using a delivery system in accordance with an embodiment of the invention.
Figure 13:
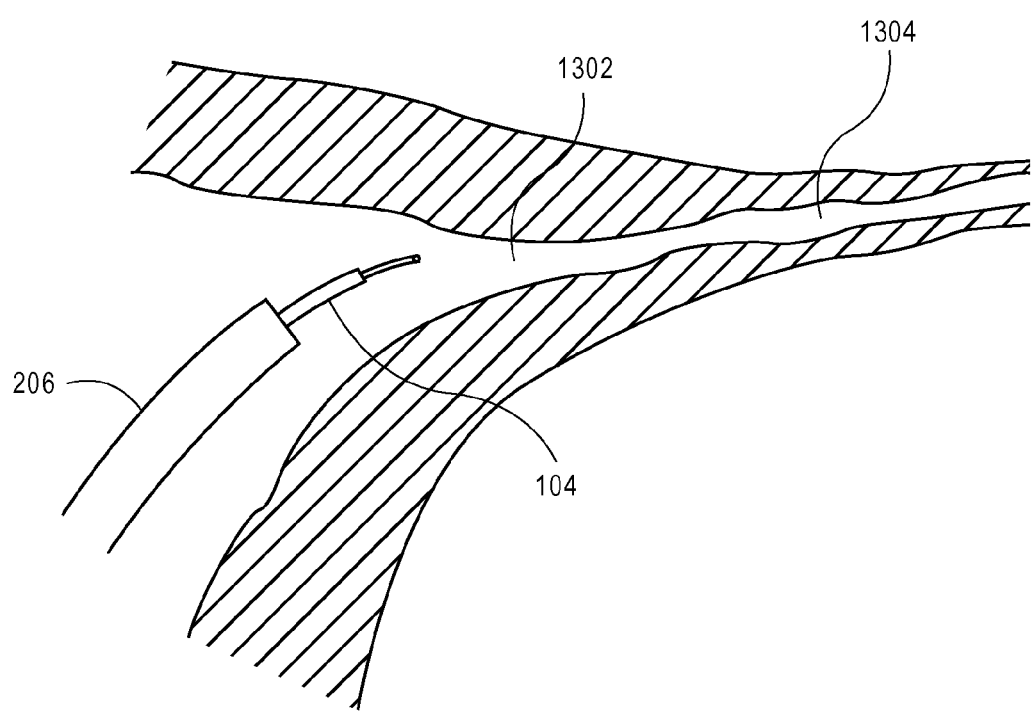
FIG. 13 is a side view of an endoscope approaching an ostium of a fallopian tube in accordance with an embodiment of the invention.

Referring to FIG. 12, a flowchart of a method for deploying an occlusion device in a fallopian tube using a delivery system is shown in accordance with an embodiment of the invention. For illustrational purposes, the following description of FIG. 12 refers to the embodiments illustrated in FIGS. 13-19. At operation 1201, a physician inserts delivery catheter 104 of delivery system 100 into working channel 204 of endoscope 206. Referring to FIG. 13, a side view of an endoscope approaching an ostium of a fallopian tube is shown in accordance with an embodiment of the invention. Delivery catheter 104 may be advanced through endoscope 206 by pushing handle assembly 500 toward working channel with one hand. As delivery catheter 104 advances, it may extend distally through a uterus and into an ostium 1302 of a fallopian tube 1304.

Referring to FIG. 14, a side view of an occlusion device in an expanded configuration is shown in accordance with an embodiment of the invention. Here, occlusion device 502 is shown as it typically exists after deployment at a targeted treatment site in fallopian tube 1304. However, it is introduced at this point in the description to illustrate some components of occlusion device 502. More specifically, occlusion device 502 may include an expandable outer coil 1402, an inner coil 1404, and a polymer fiber 1406. In an embodiment, polymer fiber 1406 may be formed from a tissue growth-promoting material, such as poly(ethylene terephthalate), to encourage tissue growth. One or both of the inner coil 1404 and outer coil 1402 may be constructed from a super elastic material, such as a nickel-titanium alloy (NiTi).

Referring again to FIG. 12, at operation 1205 the physician positions occlusion device 502 at the targeted treatment site of fallopian tube 1304. Referring to FIG. 15, a side view of an occlusion device in an unexpanded configuration coupled with a delivery catheter is shown in accordance with an embodiment of the invention. Delivery catheter 104 includes outer sheath 508 surrounding a portion of occlusion device 502. Inner coil 1404 and outer coil 1402 may be wound to a low profile such that they fit within outer sheath 508. In this unexpanded configuration, occlusion device 502 may be delivered through ostium 1302 and fallopian tube 1304.

As shown, occlusion device 502 may include a flexible tip to prevent trauma to fallopian tube 1304 during delivery. In an embodiment, a black marker 1502 on outer sheath 508 may be aligned with ostium 1302 during positioning of occlusion device 502 within fallopian tube 1304. Black marker 1502 may be viewed using endoscope 206, or in an alternative embodiment, black marker 1502 may be formed from a radiopaque material and viewed during positioning using fluoroscopy.

Referring again to FIG. 12, at operation 1210 the physician grasps endoscope 206 and distal handle 506 with first hand 304, e.g., with a right hand, as shown in FIG. 6D. After positioning occlusion device 502 at a treatment site in fallopian tube 1304, grasping both endoscope 206 and handle assembly 500 in the same hand can help to stabilize the delivery system 100, and thus occlusion device 502, relative to the treatment site. While grasping endoscope 206 and distal handle 506 with one hand, e.g., with a right hand, the physician may grasp proximal handle 504 with a second hand 306, e.g., with a left hand, as shown in FIG. 6D.

At operation 1215 the physician can move proximal handle 504 of handle assembly 500 relative to distal handle 506 through first travel 702. For example, the physician can pull proximal handle 504 with a left hand while keeping endoscope 206 and distal handle 506 stationary with a right hand. The relative movement through first travel 702 can cause outer sheath 508 to retract over occlusion device 502. More specifically, outer sheath 508 retracts as it remains operably coupled with proximal handle 504, but inner catheter 606 may remain stationary and operably coupled with distal handle 506 during first travel 634. Thus, inner catheter 606 may press against occlusion device 502 to stabilize it while outer sheath 508 is retracted.

Referring to FIG. 16A, a side view of an occlusion device in an unexpanded configuration coupled with a delivery catheter with a retracted outer catheter is shown in accordance with an embodiment of the invention. As outer sheath 508 retracts, outer coil 1402 of occlusion device 502 can become exposed to the surrounding environment, e.g., fallopian tube 1304.

Referring again to FIG. 12, at operation 1220 the physician optionally repositions occlusion device 502 relative to fallopian tube 1304. Referring to FIG. 16B, a detail view, taken of Detail X in FIG. 16A, of an occlusion device in an unexpanded configuration coupled with a delivery catheter with a retracted outer catheter is shown in accordance with an embodiment of the invention. After moving proximal handle 504 through first travel 702, outer coil 1402 may remain fully wound down and in a non-expanded state. A gold band 1602 may be used to check alignment with ostium 1302, as black marker 1502 is withdrawn with outer sheath 508. Misalignment may be corrected by releasing distal handle 506 and moving handle assembly 500 relative to endoscope 206. For example, if the system includes sleeve 640, the physician may release squeeze 648 from sleeve 640 and reposition proximal handle 504 with one hand while grasping endoscope 206 and sleeve 640 with another hand. The gold band 1602 position may be confirmed using endoscopy or fluoroscopy to ensure that occlusion device 502 is properly positioned prior to expansion. Once occlusion device 502 is properly placed, in preparation for expansion of the occlusion device 502, the physician may again grasp distal handle 506 and endoscope 206 with one hand while grasping proximal handle 504 with a another hand.

Referring again to FIG. 12, at operation 1225 the physician moves proximal handle 504 relative to distal handle 506 through second travel 704. Relative movement may be achieved, for example, by twisting proximal handle 504 relative to distal handle 506, or by some other motion consistent with the discussion above. Referring to FIG. 17, a side view of an occlusion device in a partially expanded configuration coupled with a delivery catheter is shown in accordance with an embodiment of the invention. While gold band 1602 remains aligned with ostium 1302, a release wire 1604 coupled with outer sheath 508 may be pulled in a proximal direction from outer coil 1402 to allow outer coil 1402 to unwind and/or expand. More specifically, as outer sheath 508 remains operably coupled with proximal handle 504 during second travel 704, outer sheath 508 may retract and pull on release wire 1604. In an embodiment, release wire 1604 may insert through a tab, loop, or other locking feature to prevent outer coil 1402 from prematurely unwinding and expanding. Thus, during movement through second travel 704, release wire 1604 may be at least partially retracted from the locking feature of outer coil 1402 to allow outer coil 1402 to unwind. Unwinding of outer coil 1402 may result from the release of potential energy stored within outer coil 1402 as it is wound down to the low profile. Thus, outer profile 1402 may unwind to spring outward to an expanded configuration when release wire 1604 is retracted during second travel 704.

Figure 18:
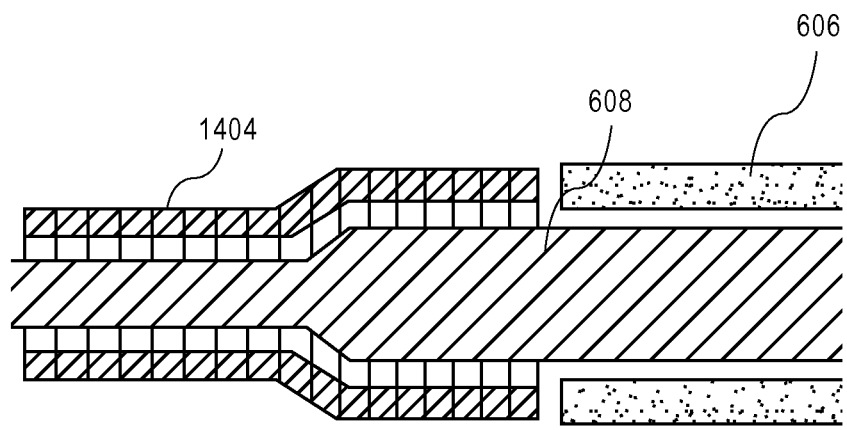
FIG. 18 is a cross-sectional view of an occlusion device coupled with a delivery wire by an interference fit in accordance with an embodiment of the invention.

Referring to FIG. 18, a cross-sectional view of an occlusion device coupled with a delivery wire by an interference fit is shown in accordance with an embodiment of the invention. Prior to movement through second travel 704, inner coil 1404 of occlusion device 502 remains attached to delivery wire 608. More specifically, inner coil 1404 may be retained in an unexpanded state due to an interference fit between inner coil 1404 and delivery wire 608. During second travel 704, as delivery wire 608 changes from being operably coupled with distal handle 506 through delivery wire mount 624 to being operably coupled with proximal handle 504 through arm 632, delivery wire 608 begins to disengage from inner coil 1404. As delivery wire 608 disengages, inner catheter 606 remains operably coupled with distal handle 506 during second travel 704, and thus, presses against a proximal end of inner coil 1404 to resist the withdrawal force applied by the interference fit with delivery wire 608.

Figure 19:
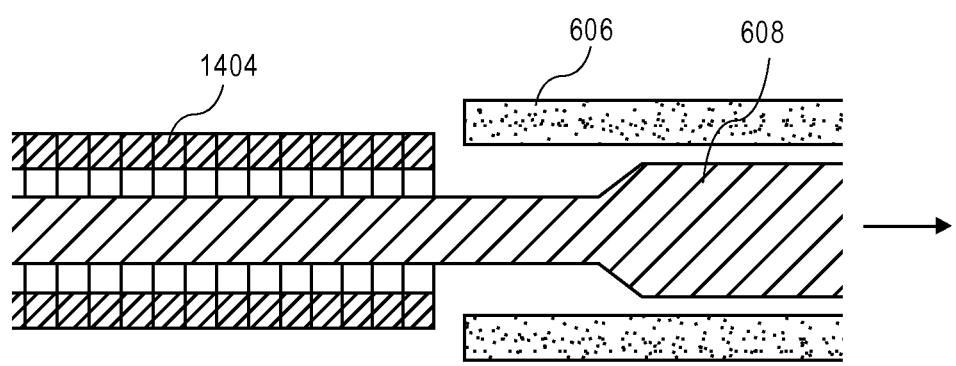
FIG. 19 is a cross-sectional view of an occlusion device uncoupled from a delivery wire in accordance with an embodiment of the invention.

Referring to FIG. 19, a cross-sectional view of an occlusion device uncoupled from a delivery wire is shown in accordance with an embodiment of the invention. As second travel 704 continues, delivery wire 608 retracts further from inner coil 1404, and the interference fit between inner coil 1404 and delivery wire 608 becomes disengaged. During disengagement, inner catheter 606 continues to press against inner coil 1404, causing occlusion device 502 to remain stationary relative to treatment site during deployment.

Following disengagement of delivery wire 608 from inner coil 1404 during second travel 704, inner coil 1404 is released into fallopian tube 1304. Thus, occlusion device 502 expands to the configuration shown in FIG. 14, with outer coil 1402 expanded against fallopian tube 1304 and polymer fiber 1406 between outer coil 1402 and inner coil 1404 to promote tissue growth within occlusion device 502. After occlusion device 502 is deployed into fallopian tube 1304, delivery catheter 104 may be withdrawn from the patient by retracting it through endoscope 206, or by removing endoscope 206 and delivery catheter 104 from the patient together.

In the foregoing specification, the invention has been described with reference to specific embodiments thereof. It will be evident that various modifications may be made to these embodiments without departing from the broader spirit and scope of the invention, as set forth in the following claims. The specification and drawings are, accordingly, to be regarded in an illustrative sense rather than a restrictive sense.

What is claimed is:

1. A delivery system comprising:
   an occlusion device;
   a delivery catheter comprising an outer sheath and a delivery wire, wherein the delivery catheter comprises an inner catheter; and
   a handle assembly comprising a distal handle slidably receiving a proximal handle, the proximal handle moveable relative to the distal handle through a first travel and a second travel, wherein the inner catheter is operably coupled with the distal handle during the first travel and the second travel, wherein relative movement between the proximal handle and the distal handle through the first travel and the second travel presses the inner catheter against the occlusion device and retracts the outer sheath over the occlusion device, and wherein relative movement through the second travel retracts the delivery wire from the occlusion device.

2. The delivery system of claim 1, wherein at least a portion of the proximal handle is exposed from the distal handle.

3. The delivery system of claim 2, wherein the distal handle comprises a channel defining the first travel and the second travel, and wherein the proximal handle comprises a nib slidably located in the channel.

4. The delivery system of claim 1, wherein the distal handle and the proximal handle are coaxially arranged, and wherein the first travel is in an axial direction.

5. The delivery system of claim 4, wherein the second travel is in a rotational direction.

6. The delivery system of claim 4, wherein the proximal handle is moveable relative to the distal handle through an intermediate travel between the first travel and the second travel, wherein the intermediate travel is in a circumferential direction, and wherein the second travel is in an axial direction.

7. The delivery system of claim 1, wherein during movement through the first travel the proximal handle is operably coupled with the outer sheath and the distal handle is operably coupled with the delivery wire, and wherein during movement through the second travel the proximal handle is operably coupled with the outer sheath and the delivery wire.

8. The delivery system of claim 1, further comprising a sleeve over a gripping surface of the distal handle, the sleeve having a flexible element normally biased away from the gripping surface, wherein the flexible element deforms toward the gripping surface under a lateral load.

9. The delivery system of claim 8, wherein the flexible element comprises one or more tabs.

10. A method comprising:
    inserting a delivery catheter of a delivery system into a lumen of an endoscope;
    positioning an occlusion device of the delivery system in a body lumen;
    moving a proximal handle of the delivery system relative to a distal handle of the delivery system through a first travel, while simultaneously grasping the endoscope and the distal handle, to expose the occlusion device to the body lumen; and
    moving the proximal handle relative to the distal handle through a second travel, while simultaneously grasping the endoscope and the distal handle, to expand the occlusion device into the body lumen.

11. The method of claim 10, wherein moving the proximal handle through the first travel comprises pulling the proximal handle relative to the distal handle.

12. The method of claim 11, wherein moving the proximal handle through the second travel comprises twisting the proximal handle relative to the distal handle.

13. The method of claim 11, wherein grasping the endoscope and the distal handle is with a first hand, and wherein pulling the proximal handle is with a second hand.

14. The method of claim 10, further comprising moving the proximal handle relative to the distal handle through an intermediate travel between the first travel and the second travel, while simultaneously grasping the endoscope and the distal handle.

15. The method of claim 14, wherein moving the proximal handle through the intermediate travel comprises twisting the proximal handle relative to the distal handle, and wherein moving the proximal handle through the second travel comprises pulling the proximal handle relative to the distal handle.

16. The method of claim 10, further comprising repositioning the occlusion device in the body lumen after moving the proximal handle through the first travel and before moving the proximal handle through the second travel.

17. The method of claim 16, wherein grasping the distal handle comprises squeezing a sleeve against the distal handle, and wherein repositioning the occlusion device comprises releasing the sleeve from the distal handle.

18. The method of claim 17, wherein squeezing the sleeve comprises squeezing a flexible element of the sleeve.

* * * * *